United States Patent [19]

Gurmarnik

[11] Patent Number: 5,257,972
[45] Date of Patent: Nov. 2, 1993

[54] DEVICE FOR AND METHOD OF LENGTH DETERMINATION OF EPIDURAL ANESTHESIA CATHETER

[76] Inventor: Simon Gurmarnik, 38 Garrison Rd., Brookline, Mass. 02146

[21] Appl. No.: 985,853

[22] Filed: Dec. 4, 1992

[51] Int. Cl.⁵ ............................................. A61M 31/00
[52] U.S. Cl. ..................................... 604/51; 604/117; 604/158; 128/898
[58] Field of Search ............... 604/116, 117, 164, 158, 604/173, 264, 280, 49, 51, 27, 28; 128/898, 774

[56] References Cited

U.S. PATENT DOCUMENTS

| | | | |
|---|---|---|---|
| 3,213,541 | 10/1965 | Raffman | 128/774 |
| 4,500,313 | 2/1985 | Young | 128/774 |
| 4,563,176 | 1/1986 | Gustavsson et al. | 604/280 |
| 4,863,423 | 9/1989 | Wallace | 604/280 |
| 4,940,458 | 7/1990 | Cohn | 604/158 |
| 4,973,305 | 11/1990 | Goltzer | 604/158 |
| 5,106,376 | 4/1992 | Mononen et al. | 604/164 |
| 5,129,889 | 7/1992 | Hahn et al. | 604/51 |
| 5,163,927 | 11/1992 | Woker et al. | 604/96 |

*Primary Examiner*—C. Fred Rosenbaum
*Assistant Examiner*—Ronald Stright, Jr.
*Attorney, Agent, or Firm*—Ilya Zborovsky

[57] ABSTRACT

A device and a method for determining a required length of an epidural catheter for a continuous epidural anesthesia, has an element formed as a ruler and having two opposite sides, a shorter scale provided on one side of the ruler and having a length substantially corresponding to a length of an epidural needle, and a longer scale provided on the other side of the ruler and being longer than the shorter scale by a length corresponding to a required length of an epidural catheter inside an epidural space, so that when an epidural needle is inserted in the epidural space and the ruler is placed against the skin parallel to the epidural needle, then when an epidural catheter is placed parallel to the ruler extending from a hub of the epidural needle along the longer scale, its length between the hub of the epidural needle and a beginning of the longer scale corresponds to a required length of the epidural catheter to be inserted into a patient.

1 Claim, 1 Drawing Sheet

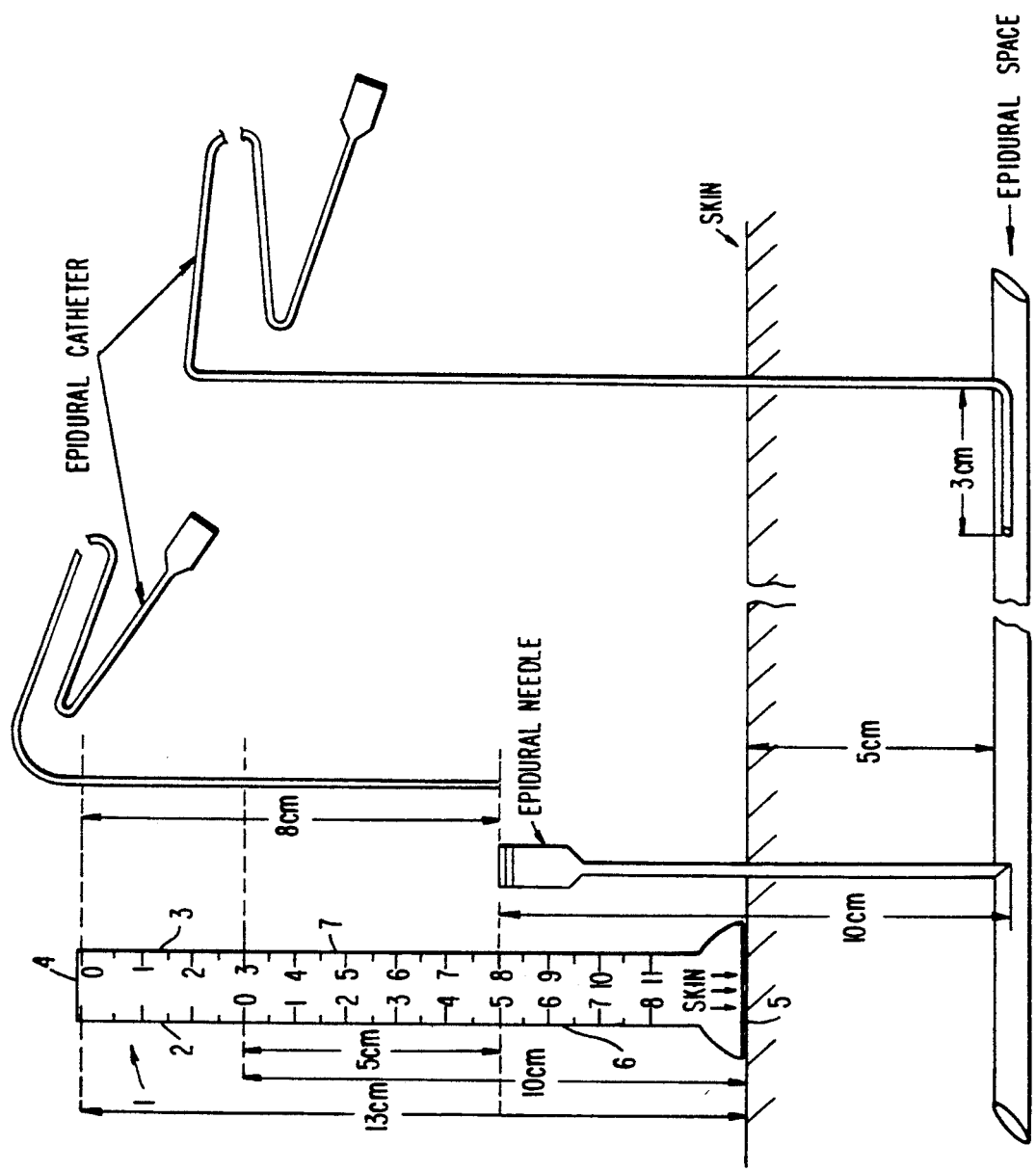

DEVICE FOR AND METHOD OF LENGTH DETERMINATION OF EPIDURAL ANESTHESIA CATHETER

BACKGROUND OF THE INVENTION

The present invention relates to a device and method for determination of a required length of an epidural catheter for continuous epidural anesthesia.

It is known that a standard procedure for the continuous epidural anesthesia requires localization of the epidural space by the epidural needle, then insertion of the epidural catheter through the epidural needle, then removal of the epidural needle and positioning of the catheter within the epidural space. Proper positioning of the epidural catheter is 2.5-3 cm inside the epidural space, and this proper position will minimize occurence of complications. Since the distance between the skin and the epidural space varies from 3 to 8 cm, every case requires a time consuming calculation of the length of the catheter with the graduated epidural needle and catheter.

It is known that in this procedure for a continuous epidural anesthesia when the epidural catheter is utilized, the catheter in the epidural space can be the cause of various iatrogenic complications. In order to avoid leaving too great a length in the lumbar epidural space during epidural anesthesia, graduated Tuochy needles can be used together with graduated epidural catheters. On the latter, a special marking shows that, when it reaches the needle hub, the catheter tip is at the needle bevel. Approximately 5-7 cm of the catheter length is introduced into the epidural space. The needle is removed and placed upside down next to the catheter with the hub in contact with the patient's skin. In this position the distance between the special marking on the catheter and the graduation on the needle which marks the skin level is equivalent to the length of the catheter in the epidural space. This distance and therefore the catheter length can then be reduced to about 4 cm by carefully withdrawing the catheter. Knowing exactly how much of the catheter is within the epidural space can be of particular importance whenever that space is uncommonly far from the patient's skin, due to obesity, oedema, use of paramedian route or a very oblique angle of the needle in the sagittal plane. The above described method is quite complicated and it is to be understood that it is desirable to improve the same.

In the stressful atmosphere of the operating room the above specified measurements and calculations present unnecessary hardships and usually are done with a great degree of inaccuracy.

SUMMARY OF THE INVENTION

Accordingly, it is an object of the present invention to provide a device for and a method of determination of a required length of the epidural catheter for continuous epidural anesthesia, which avoids the disadvantages of the prior art.

In keeping with these objects and with others which will become apparent hereinafter, one feature of the present invention resides, briefly stated, in a device for determination of a required length of an epidural catheter for continuous epidural anesthesia, which is formed as a ruler having two scales of different lengths, wherein one scale corresponds to a length of the epidural needle, while the other scale is longer than the one scale by a length corresponding to a required length of the epidural catheter inside the epidural space.

When the device is designed in accordance with the present invention it is substantially simpler to determine the required length of the epidural catheter by positioning the device on the skin and then placing the epidural catheter so that it extends from the hub of the epidural needle and therefore its required length is determined on the second longer scale.

The device makes significantly simpler the determination of the required length of the epidural catheter.

In accordance with another feature of the present invention, a method of length determination of the epidural catheter is proposed, in which the epidural needle is introduced into the epidural space, then the device having the above mentioned two scales is placed against the skin parallel to the epidural needle, and the catheter is positioned from the hub of the epidural needle along the longer scale so that the required length of the epidural catheter is immediately determined on the longer scale.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a view illustrating a method of determination of a required length of the epidural catheter for continuous epidural anesthesia and the epidural catheter measured by the inventive device and introduced into the epidural space.

DESCRIPTION OF THE PREFERRED EMBODIMENTS

A device for determination of the required length of an epidural catheter for continuous epidural anesthesia is formed as a ruler which is identified as a whole with reference numeral 1. The ruler is formed as an elongated member having two opposite sides 2 and 3, a top 4 and a bottom 5. One side 2 of the ruler is provided with a shorter scale 6 while the other side 3 of the ruler is provided with a longer scale 7.

The bottom 5 of the ruler 1 is used for placement of the ruler against a skin. The shorter scale is substantially equal to the total length of the epidural needle. It is used for instant determination of the distance between the skin and the epidural space, or in other words the distance from zero on the shorter scale 6 to the hub of the epidural needle.

The longer scale 7 is longer than the epidural needle and is used for the instant determination of the required length of the epidural catheter. The longer scale 7 is longer than the shorter scale 6 by the required length of the epidural catheter inside the epidural space. The longer scale determines the required length of the epidural catheter which is equal to the distance from zero on the longer scale 7 to the hub of the epidural needle.

In the shown embodiment the shorter scale 6 is equal to 10 cm, while the longer scale 7 is equal to 13 cm, since the required length of the epidural catheter inside the epidural space is selected to be 3 cm.

The procedure of continuous epidural anesthesia with the device in accordance with the present invention is the same. In other words first the epidural space is localized by the epidural needle, then the epidural catheter is inserted through the epidural needle, then the epidural needle is removed, and the catheter is positioned within the epidural space. The determination of the required length of the catheter is performed in the following manner. When the epidural needle is inserted into the epidural space as shown in FIG. 1, the ruler 1 is placed against the skin parallel to the epidural needle. Then the epidural catheter is positioned so that it extends from the hub of the epidural needle along the longer scale, and the required length of the epidural catheter can be immediately determined on the longer scale as shown in the drawing. In the shown example it has to be equal to 8 cm.

It will be understood that each of the elements described above, or two or more together, may also find a useful application in other types of constructions and methods differing from the types described above.

While the invention has been illustrated and described as embodied in a device and a method for length determination of the epidural catheter for the continuous epidural anesthesia, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method of determining a required length of an epidural catheter for a continuous epidural anesthesia, comprising the steps of providing an element formed as a ruler having a shorter scale on its one side with a length corresponding to a length of an epidural needle and a longer scale on its other side which is longer than the shorter scale by a length corresponding to the required length of the epidural catheter inside an epidural space; inserting an epidural needle into an epidural space; placing said ruler against a skin parallel to said epidural needle; and placing an epidural catheter from a hub of said epidural needle along said longer scale, so that a distance from the hub of the epidural needle to a beginning of said longer scale corresponds to a required length of the epidural catheter to be inserted into a patient.

* * * * *